(12) United States Patent
Byun et al.

(10) Patent No.: US 12,171,560 B2
(45) Date of Patent: Dec. 24, 2024

(54) PIXEL CIRCUIT FOR RADIATING STIMULATION SIGNAL AND RECEIVING BIOSIGNAL AND ELECTRONIC DEVICE INCLUDING THE SAME

(71) Applicant: ELECTRONICS AND TELECOMMUNICATIONS RESEARCH INSTITUTE, Daejeon (KR)

(72) Inventors: Chunwon Byun, Daejeon (KR); O Eun Kwon, Daejeon (KR); Chan Woo Park, Daejeon (KR); Hyunkoo Lee, Daejeon (KR); Sukyung Choi, Daejeon (KR); Chan-Mo Kang, Daejeon (KR); Byoung-Hwa Kwon, Daejeon (KR); Chil Seong Ah, Daejeon (KR); Hyunsu Cho, Daejeon (KR); Jeong Ik Lee, Daejeon (KR); Nam Sung Cho, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1098 days.

(21) Appl. No.: 16/852,648

(22) Filed: Apr. 20, 2020

(65) Prior Publication Data

US 2020/0352460 A1 Nov. 12, 2020

(30) Foreign Application Priority Data

May 7, 2019 (KR) ........................ 10-2019-0052743

(51) Int. Cl.
*A61B 5/30* (2021.01)
*A61B 5/291* (2021.01)

(52) U.S. Cl.
CPC ................ *A61B 5/30* (2021.01); *A61B 5/291* (2021.01); *A61B 2562/046* (2013.01)

(58) Field of Classification Search
CPC ..... A61B 5/30; A61B 5/291; A61B 2562/046; A61B 5/0031; A61B 5/369; A61N 5/0622;

(Continued)

(56) References Cited

U.S. PATENT DOCUMENTS 7,917,201 B2 3/2011 Gozani et al.
8,267,862 B2 9/2012 Jeong et al.
(Continued)

FOREIGN PATENT DOCUMENTS

EP 2632388 A2 9/2013
KR 10-1007558 B1 1/2011
(Continued)

OTHER PUBLICATIONS

De Waal et al. (Implementation of A Portable Pattern Stimulator and Vep/Erg Recording System Based on an Apple Microcomputer, Doc. Ophthal. Proc. Series, vol. 37, pp. 209-216 (Year: 1983).*

*Primary Examiner* — Jacqueline Cheng
*Assistant Examiner* — Tho Q Tran
(74) *Attorney, Agent, or Firm* — Rabin & Berdo, P.C.

(57) ABSTRACT

A pixel circuit includes a sensing block, a stimulation block, a first line control circuit, and a second line control circuit. The sensing block outputs biometric data of a biosignal in response to a first selection signal. The stimulation block radiates a stimulation signal in response to a second selection signal. The first line control circuit outputs the first selection signal for selecting the sensing block as a target sensing block, and outputs the second selection signal for selecting the stimulation block as a target stimulation block. The second line control circuit processes characteristic data associated with the biometric data and the stimulation signal.

10 Claims, 10 Drawing Sheets

(58) Field of Classification Search
CPC .......... A61N 1/04; A61N 1/08; A61N 5/0601; A61N 7/00; A61N 2005/0626; A61N 2007/0026
See application file for complete search history.

(56) References Cited

U.S. PATENT DOCUMENTS

| | | |
|---|---|---|
| 8,798,707 B2 | 8/2014 | Choi et al. |
| 10,390,756 B2 | 8/2019 | Youm et al. |
| 2008/0303554 A1* | 12/2008 | Chiang .............. H03K 19/0008 326/104 |
| 2012/0253166 A1 | 10/2012 | Ahn et al. |
| 2013/0175941 A1* | 7/2013 | Wu ........................ H05B 45/60 315/226 |
| 2016/0331994 A1 | 11/2016 | Smith et al. |
| 2018/0333587 A1* | 11/2018 | Howard ............... A61B 5/0006 |

FOREIGN PATENT DOCUMENTS

| | | |
|---|---|---|
| KR | 101645573 B1 | 8/2016 |
| KR | 101648463 B1 | 8/2016 |
| KR | 10-1749511 B1 | 6/2017 |
| KR | 20170099030 A | 8/2017 |
| KR | 10-2018-0061826 A | 6/2018 |
| KR | 20190031941 A | 3/2019 |

* cited by examiner

PIXEL CIRCUIT FOR RADIATING STIMULATION SIGNAL AND RECEIVING BIOSIGNAL AND ELECTRONIC DEVICE INCLUDING THE SAME

CROSS-REFERENCE TO RELATED APPLICATIONS

This U.S. non-provisional patent application claims priority under 35 U.S.C. § 119 of Korean Patent Application No. 10-2019-0052743, filed on May 7, 2019, the entire contents of which are hereby incorporated by reference.

BACKGROUND

Embodiments of the inventive concept relate to a pixel circuit and an electronic device, and more particularly, relate to a pixel circuit and an electronic device for insertion into a living body.

As medical industry develops, technologies in a field of information and communication industry are applied to the medical industry. For example, to meet needs of the medical industry for more accurate diagnosis and more precise treatment, research on various information communication devices and semiconductor chips is in progress.

A living body, such as a human body, radiates various types of biosignals. As an example, the human brain radiates brain waves that may be classified as a type of electrical signal. The brain waves are a standard for understanding a state of brain activity. Accordingly, in brain science research, precise measurements of the brain waves may be required. To this end, research on an electronic device that is configured to sense the biosignals is being conducted.

To treat a disease that is diagnosed, a device for stimulating the human body is used. For example, brain neurological disease may be alleviated in the case where various types of physical signals (e.g., light, electricity, ultrasound, etc.) are used to stimulate specific areas of a brain. Therefore, research is being conducted on an electronic device that generates a signal for stimulating the human body.

SUMMARY

Embodiments according to the inventive concept provide a pixel circuit and an electronic device that are configured to radiate a signal for stimulating a living body and to receive a biosignal.

A pixel circuit according to an embodiment of the inventive concept may include a sensing block, a stimulation block, a first line control circuit, and a second line control circuit. The sensing block may output biometric data of a biosignal in response to a first selection signal. The stimulation block may radiate a stimulation signal in response to a second selection signal. The first line control circuit may output the first selection signal for selecting the sensing block as a target sensing block, and may output the second selection signal for selecting the stimulation block as a target stimulation block. The second line control circuit may process characteristic data associated with the biometric data and the stimulation signal.

An electronic device according to an embodiment of the inventive concept may include a pixel array circuit and a first line control circuit. The pixel array circuit may radiate a stimulation signal by a target pixel that is selected in response to a first logic value of a first selection signal, and may output biometric data of a biosignal by the target pixel that is selected in response to a second logic value of a second selection signal. The first line control circuit may generate the first selection signal and the second selection signal. The pixel array circuit and the first line control circuit are disposed on one substrate.

An electronic device according to an embodiment of the inventive concept may include a unit pixel and a line control circuit. The unit pixel may include a reference voltage electrode circuit that generates a reference voltage associated with radiating a stimulation signal and receiving a biosignal, and a plurality of pixel circuits that radiates the stimulation signal in response to a first logic value of a first selection signal and outputs biometric data of the biosignal in response to a second logic value of a second selection signal. The line control circuit may output the first selection signal and the second selection signal for selecting the unit pixel as a target pixel. The reference voltage may be shared by the plurality of pixel circuits such that the stimulation signal is radiated and the biometric data are processed.

BRIEF DESCRIPTION OF THE FIGURES

The above and other objects and features of the inventive concept will become apparent by describing in detail exemplary embodiments thereof with reference to the accompanying drawings.

DETAILED DESCRIPTION

Embodiments of the inventive concept will be described below in more detail with reference to the accompanying drawings. In the following descriptions, details such as detailed configurations and structures are provided merely to assist in an overall understanding of embodiments of the inventive concept. Modifications of the embodiments described herein can be made by those skilled in the art without departing from the spirit and scope of the inventive concept. Furthermore, descriptions of well-known functions and structures are omitted for clarity and brevity. The terms used in this specification are defined in consideration of the functions of the inventive concept and are not limited to specific functions. Definitions of terms may be determined based on the description in the detailed description.

In the following drawings or the detailed description, circuits may be connected to others in addition to the components illustrated in drawing or described in the detailed description. The circuits or components may be directly or indirectly connected. The circuits or components may be communicatively connected or may be physically connected.

Unless defined otherwise, all terms including technical and scientific terms used herein have the same meaning as can be understood by one of ordinary skill in the art to which the inventive concept belongs. Generally, terms defined in the dictionary are interpreted to have equivalent meaning to the contextual meanings in the related art and are not to be construed as having ideal or overly formal meaning unless expressly defined in the text.

Figure 1:
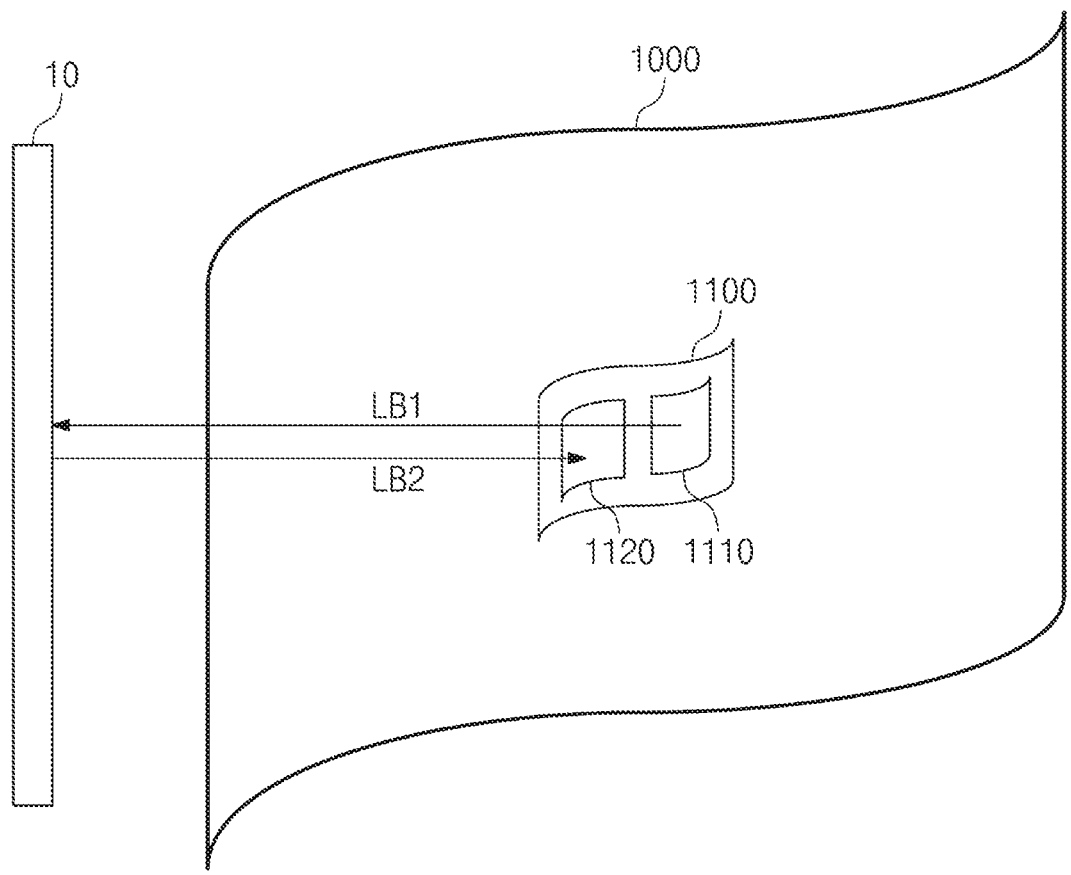
FIG. 1 is a conceptual diagram illustrating an exemplary operation of an active complex array circuit according to an embodiment of the inventive concept.

FIG. 1 is a conceptual diagram illustrating an exemplary operation of an active complex array circuit according to an embodiment of the inventive concept.

Referring to FIG. 1, an active complex array circuit 1000 may include a pixel circuit 1100. The pixel circuit 1100 may include a biosignal stimulation device 1110 and a biosignal sensing device 1120. For better understanding, only one pixel circuit 1100 is illustrated, but it will be understood that the active complex array circuit 1000 has a plurality of pixel circuits including the pixel circuit 1100. Configurations and operations of each of the plurality of pixel circuits that is included in the active complex array circuit 1000 are similar to those of the pixel circuit 1100, respectively, and thus, redundant descriptions below will be omitted to avoid redundancy.

The biosignal stimulation device 1110 may generate a transmitting signal LB1 to be radiated toward an object 10. The biosignal stimulation device 1110 may radiate the transmitting signal LB1 toward the object 10. For example, the object 10 may be part or all of a living body, such as organs, blood vessels, skin, etc. of a human body.

As an example, the transmitting signal LB1 may be a stimulation signal that is radiated for stimulation of part or all of the human body. For example, the transmitting signal LB1 may be used for the purpose of treating the human body by stimulating part or all of the human body. The transmitting signal LB1 may be implemented as at least one of various types of signals such as visible light, infrared light, ultraviolet light, ultrasonic waves, radio waves, etc. In addition, the biosignal stimulation device 1110 may be implemented with at least one of various signal generating devices, such as a light source generating device and an ultrasonic wave generating device, to generate various types of signals.

A receiving signal LB2 generated by the object 10 may be provided to the biosignal sensing device 1120. For example, the receiving signal LB2 may be various types of biosignals that are generated by the living body. For example, the receiving signal LB2 may be a brain wave generated from a human brain. Since the receiving signal LB2 is generated by the object 10, the receiving signal LB2 may include information related to the object 10. For example, the receiving signal LB2 may include information related to an active state of a brain.

The active complex array circuit 1000 may be implemented on a flexible substrate that is easily deformed in shape such that the active complex array circuit 1000 may be inserted into an inside of human body having an irregular shape. For example, the active complex array circuit 1000 may include thin film transistors (TFTs) implemented on the flexible substrate.

Figure 2:
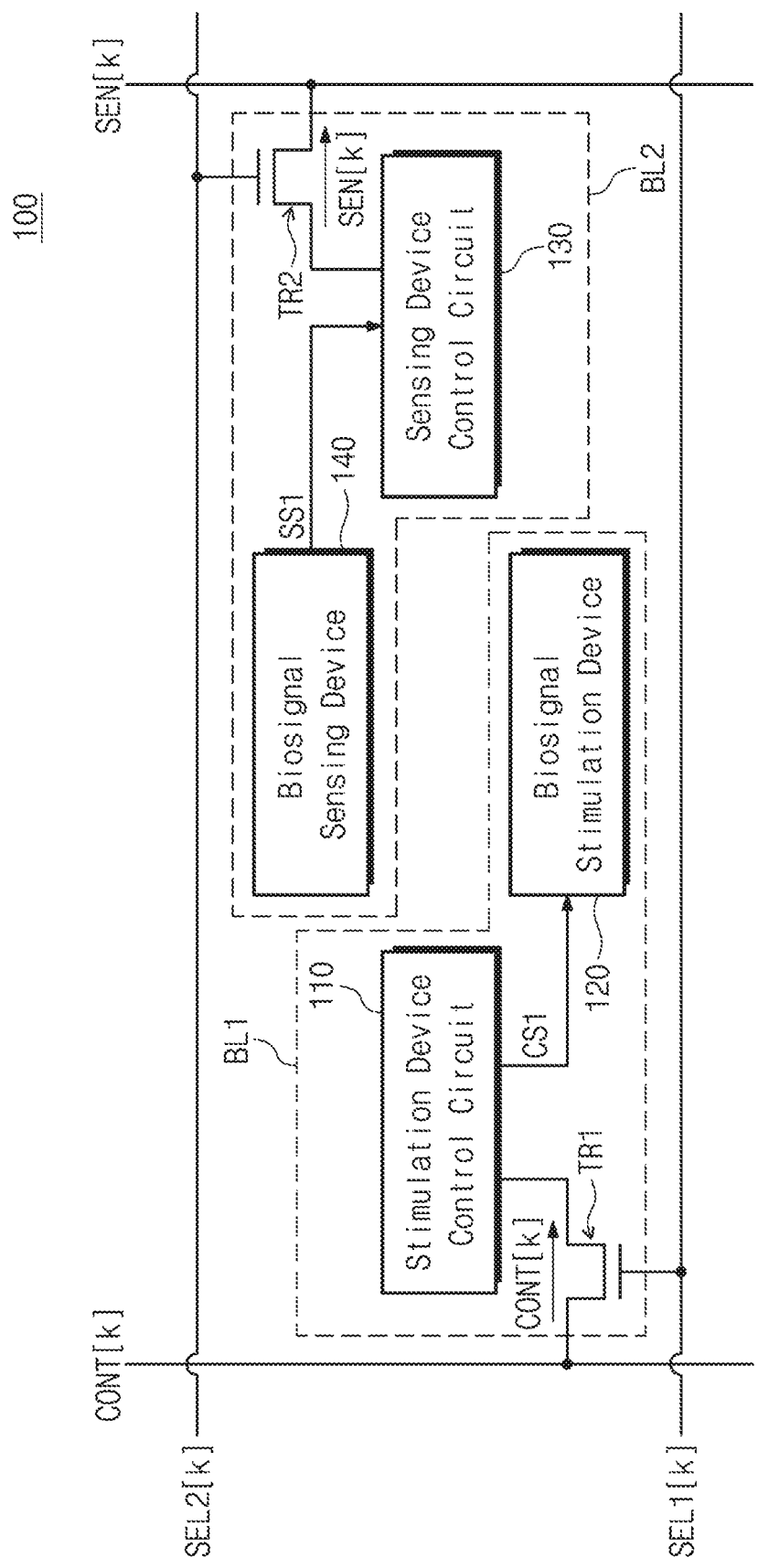
FIG. 2 is a block diagram illustrating an exemplary configuration of a pixel circuit according to an embodiment of the inventive concept.

FIG. 2 is a block diagram illustrating an exemplary configuration of a pixel circuit according to an embodiment of the inventive concept.

Referring to FIG. 2, a pixel circuit 100 may include a stimulation block BL1 and a sensing block BL2. The stimulation block BL1 may include a stimulation device control circuit 110, a biosignal stimulation device 120, and a transistor TR1. The sensing block BL2 may include a sensing device control circuit 130, a biosignal sensing device 140, and a transistor TR2.

The transistors TR1 and TR2 may be implemented with various types of transistors, respectively. For example, each of the transistors TR1 and TR2 may be implemented as one of transistors that operate according to various operating principles, such as a bipolar junction transistor (BJT), a field effect transistor (FET), etc. Alternatively, the transistors TR1 and TR2 may be implemented as a thin film transistor, respectively.

The transistors TR1 and TR2 may perform a switching operation in the pixel circuit 100. When the transistors TR1 and TR2 are turned on, a signal may be transferred through the transistors TR1 and TR2. When the transistors TR1 and TR2 are turned off, the signal may be blocked by the transistors TR1 and TR2.

For example, each of the transistors TR1 and TR2 may be implemented as an n-type thin film transistor that is turned on in response to a logic value "1" and turned off in response to a logic value "0", but the inventive concept is not limited thereto. The transistors TR1 and TR2 may be implemented with various types of devices that may be used for the switching operation.

A gate terminal of the transistor TR1 may be connected to a line of a selection signal SEL1[$k$]. The transistor TR1 may be connected between a line of a signal CONT[$k$] and the stimulation device control circuit 110. The stimulation device control circuit 110 may receive the signal CONT[$k$] related to control of the biosignal stimulation device 120 from the line of the signal CONT[$k$] through the transistor TR1. The stimulation device control circuit 110 may generate a signal CS1 for controlling the biosignal stimulation device 120, based on the signal CONT[$k$]. The stimulation device control circuit 110 may output the signal CS1 to the biosignal stimulation device 120.

For example, the biosignal stimulation device 120 may radiate the transmitting signal LB2 for stimulating the living body, etc. to an outside of the pixel circuit 100, based on the signal CS1. The biosignal stimulation device 120 may include a passive device (e.g., a light source device) for radiating the transmitting signal LB2.

A gate terminal of the transistor TR2 may be connected to a line of a selection signal SEL2[$k$]. The transistor TR2 may be connected between a line of a signal SEN[$k$] and the sensing device control circuit 130. The biosignal sensing device 140 may generate a signal SS1 for transferring data represented by a signal (e.g., the receiving signal LB2 of FIG. 1), based on the signal received from the outside of the pixel circuit 100. For example, the biosignal sensing device 140 may include a passive device (e.g., a photosensitive device) that senses the receiving signal LB2 and generates the signal SS1. The biosignal sensing device 140 may output the signal SS1 to the sensing device control circuit 130.

The sensing device control circuit 130 may generate the signal SEN[$k$] including information sensed by the biosignal sensing device 140, based on the signal SS1. For example, the sensing device control circuit 130 may generate the signal SEN[$k$] representing data of the receiving signal LB2.

The sensing device control circuit 130 may output the signal SEN[k] to the line of the signal SEN[k] through the transistor TR2.

As an example, the pixel circuit 100 may be a "k"-th pixel circuit (where, the "k" is a natural number) disposed in any row and any column of the plurality of pixel circuits that constitute the active complex array circuit 1000. As will be described with reference to FIGS. 7 and 8, the line of the selection signal SEL1[k] and the line of the selection signal SEL2[k] may be connected to a row line control circuit for controlling the active complex array circuit 1000 including the pixel circuit 100 in units of a row. In addition, the line of the signal CONT[k] and the line of the signal SEN[k] may be connected to a column line control circuit for controlling the active complex array circuit 1000 including the pixel circuit 100 in units of a column.

Exemplary operations of the pixel circuit 100 will be described in more detail below with reference to FIGS. 3 and 4.

Figure 3:
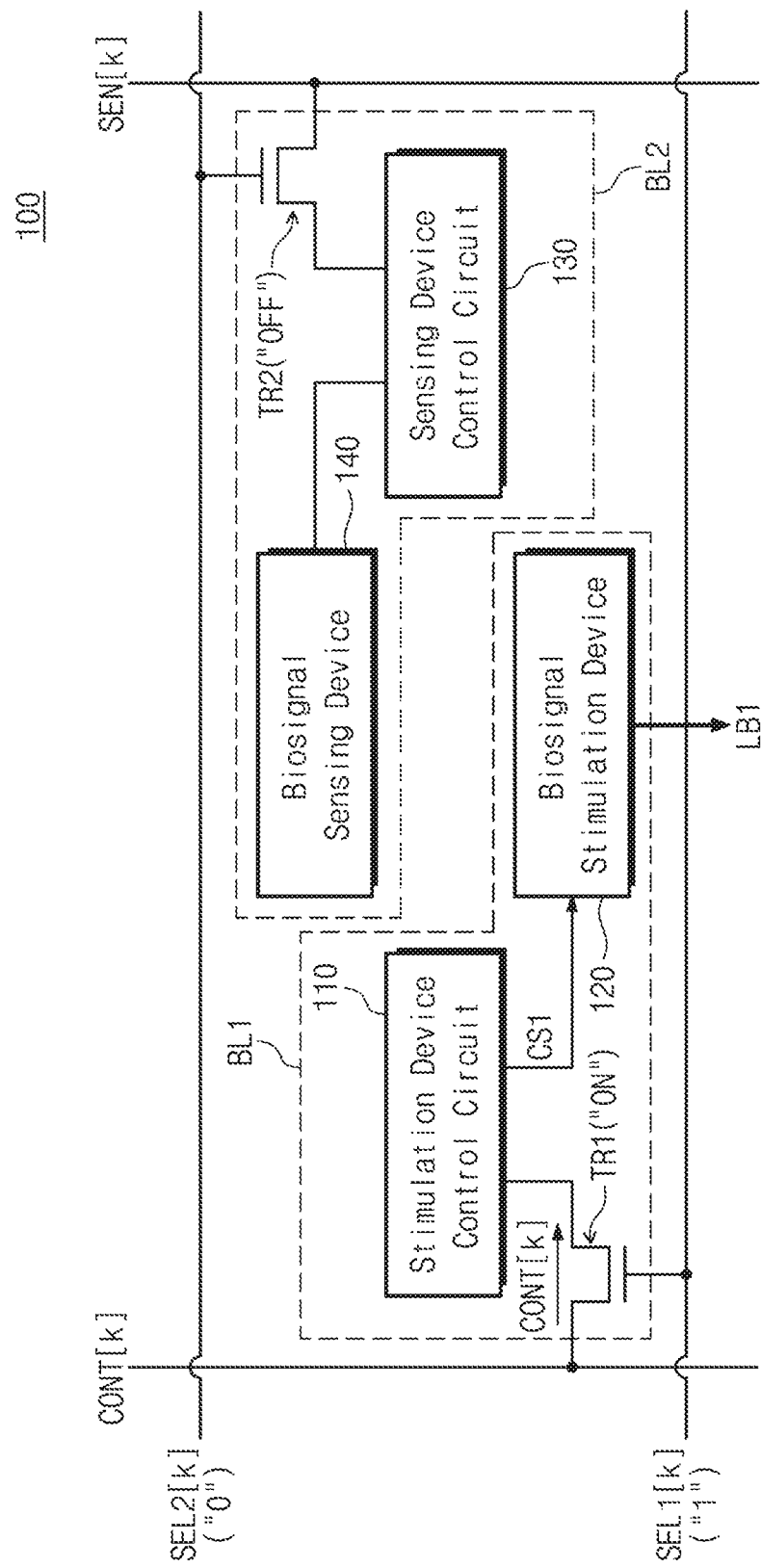
FIG. 3 is a block diagram illustrating exemplary operations of a pixel circuit of FIG. 2.

FIG. 3 is a block diagram illustrating exemplary operations of a pixel circuit of FIG. 2. Hereinafter, exemplary operations of the pixel circuit 100 for radiating the transmitting signal LB1 in response to the selection signal SEL1[k] will be described with reference to FIG. 3.

As will be described with reference to FIGS. 7 and 8, the active complex array circuit 1000 may include the plurality of pixel circuits having a configuration similar to that of the pixel circuit 100. For example, the pixel circuit 100 may be selected as a target pixel circuit by an electronic device external to the pixel circuit 100, such as a processor. The row line control circuit may output the selection signal SEL1[k] for controlling the pixel circuit 100 under control of the processor.

In an example of FIG. 3, the row line control circuit external to the pixel circuit 100 may output a signal having the logic value "1" through the line of the selection signal SEL1[k] to control the biosignal stimulation device 120. The transistor TR1 may receive the selection signal SEL1[k] having the logic value "1" from the line of the selection signal SEL1[k] through the gate terminal. The transistor TR1 may be turned on in response to the logic value "1" of the selection signal SEL1[k] that is received through the gate terminal.

The column line control circuit external to the pixel circuit 100 may output the signal CONT[k] through the line of the signal CONT[k] to control the biosignal stimulation device 120 in the pixel circuit 100. The stimulation device control circuit 110 may receive the signal CONT[k] from the line of the signal CONT[k] through the transistor TR1 that is turned on. The stimulation device control circuit 110 may output the signal CS1 for controlling the biosignal stimulation device 120 to the biosignal stimulation device 120 in response to the signal CONT[k].

As an example, the stimulation device control circuit 110 may generate the signal CS1 for controlling characteristics of the transmitting signal LB1 that is radiated from the biosignal stimulation device 120, based on the signal CONT[k]. For example, the biosignal stimulation device 120 may be implemented as a light source, and the transmitting signal LB1 may be implemented with light. The signal CONT[k] may include information related to a frequency and/or a level of the transmitting signal LB1. The stimulation device control circuit 110 may output the signal CS1 for adjusting the frequency and/or the level of the transmitting signal LB1 to the biosignal stimulation device 120, based on the signal CONT[k].

The biosignal stimulation device 120 may receive the signal CS1 from the stimulation device control circuit 110. The biosignal stimulation device 120 may generate the transmitting signal LB1 having characteristics (e.g., frequency and/or level) determined based on the signal CS1. The biosignal stimulation device 120 may radiate the transmitting signal LB1 to the outside of the pixel circuit 100. For example, the biosignal stimulation device 120 may radiate the transmitting signal LB1 to a part of the human body such as the brain.

Figure 4:
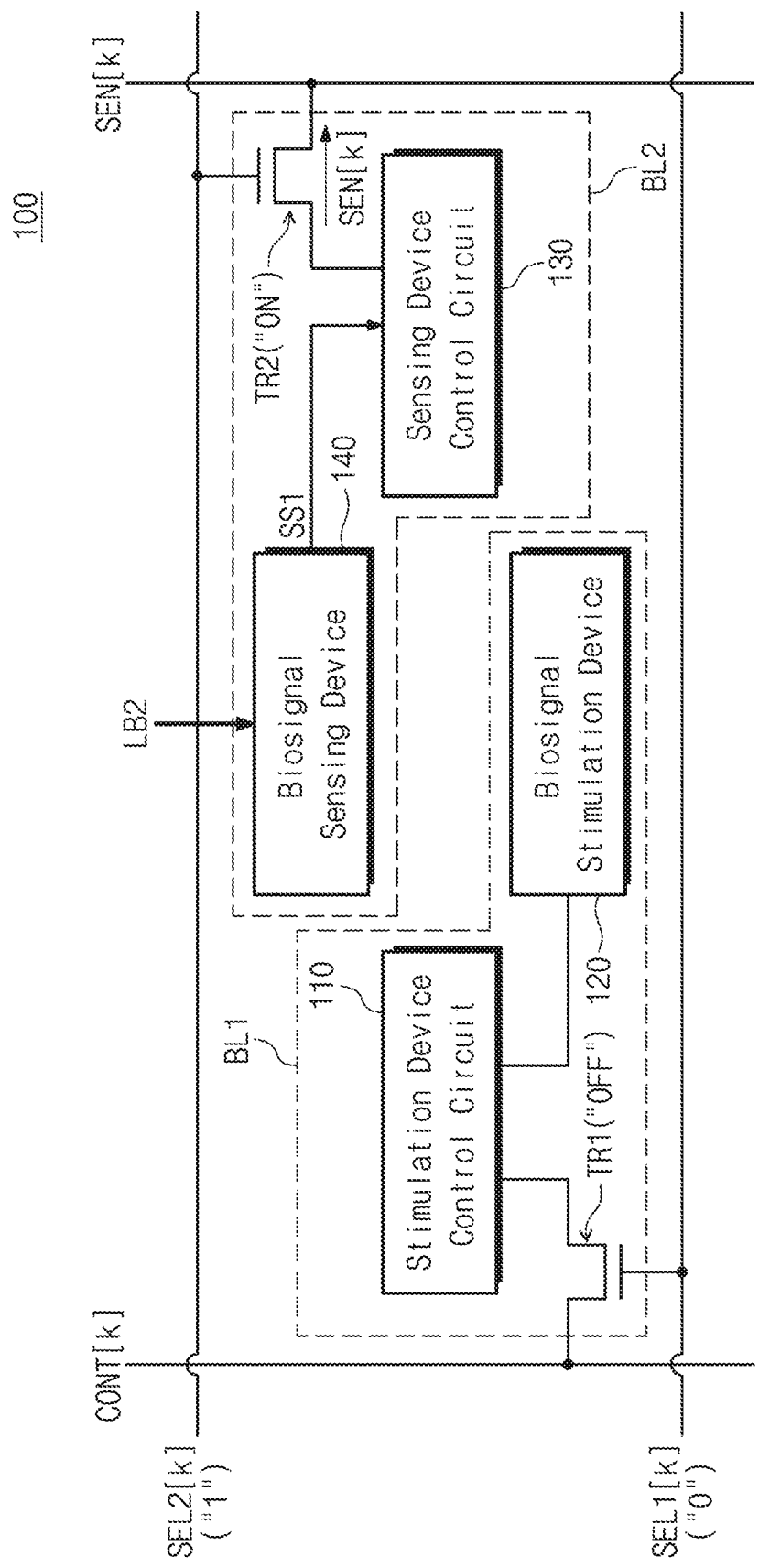
FIG. 4 is a block diagram illustrating exemplary operations of a pixel circuit of FIG. 2.

FIG. 4 is a block diagram illustrating exemplary operations of a pixel circuit of FIG. 2. Hereinafter, referring to FIG. 4, exemplary operations of the pixel circuit 100 for receiving the receiving signal LB2 and for outputting data represented by the receiving signal LB2 in response to the selection signal SEL2[k] will be described.

In an example of FIG. 4, the row line control circuit external to the pixel circuit 100 may transmit the selection signal SEL2[k] having the logic value "1" through the line of the selection signal SEL2[k] connected to the pixel circuit 100 to control the biosignal sensing device 140 of the pixel circuit 100. The transistor TR2 may receive the selection signal SEL2[k] having the logic value "1" from the line of the selection signal SEL2[k] through the gate terminal. The transistor TR2 may be turned on in response to the logic value "1" of the selection signal SEL2[k] that is received through the gate terminal.

As described with reference to FIG. 1, the biosignal sensing device 140 may receive a receiving signal LB2 from the outside of the pixel circuit 100. For example, the biosignal sensing device 140 may be implemented as an electrode for sensing the brain wave. The receiving signal LB2 may include information related to the object 10.

The biosignal sensing device 140 may generate the signal SS1 to transfer information of the object 10 included in the receiving signal LB2. For example, the biosignal sensing device 140 may generate the signal SEN[k] that represents data (i.e., data representing information of the object 10) of the signal LB2. As an example, the signal SEN[k] may represent data related to the active state of the brain.

The sensing device control circuit 130 may receive the signal SS1 from the biosignal sensing device 140. The sensing device control circuit 130 may perform various processing on the signal SS1 to effectively transfer the information of the object 10. For example, the sensing device control circuit 130 may generate the signal SEN[k] by sampling the signal SS1. The sensing device control circuit 130 may output the signal SEN[k] to the line of the signal SEN[k] through the transistor TR2 that is turned on. The signal SEN[k] may be transmitted to the column line control circuit external to the pixel circuit 100 through the line of the signal SEN[k].

Figure 5:
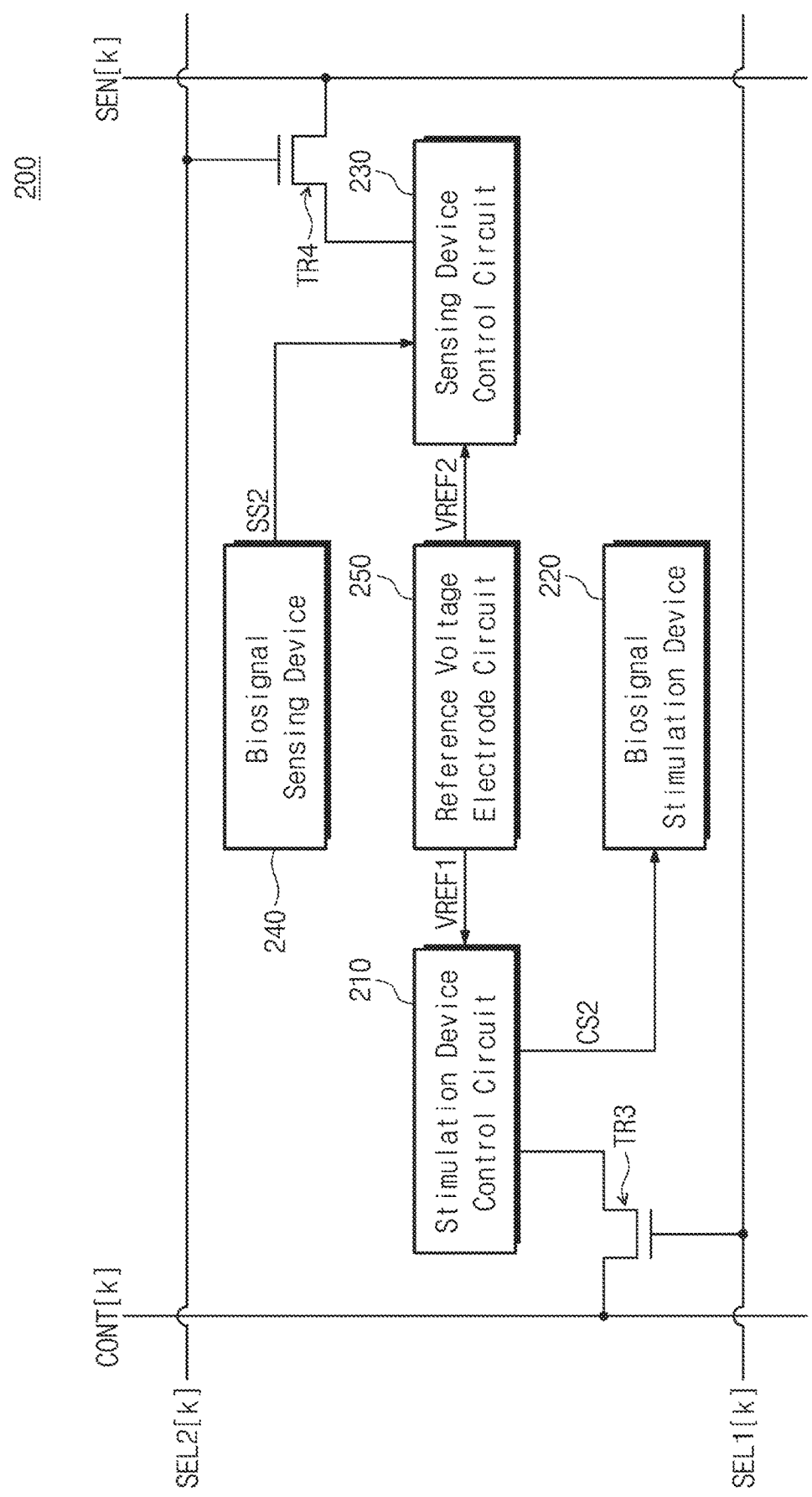
FIG. 5 is a block diagram illustrating an exemplary configuration of a pixel circuit according to an embodiment of the inventive concept.

FIG. 5 is a block diagram illustrating an exemplary configuration of a pixel circuit according to an embodiment of the inventive concept.

Comparing a pixel circuit 200 of FIG. 5 with the pixel circuit 100 of FIG. 2, configurations and operations of a stimulation device control circuit 210, a biosignal stimulation device 220, a sensing device control circuit 230, a biosignal sensing device 240, and transistors TR3 and TR4 of the pixel circuit 200 may correspond configurations and operations of the stimulation device control circuit 110, the biosignal stimulation device 120, the sensing device control circuit 130, the biosignal sensing device 140, and the transistors TR1 and TR2 of FIG. 2, respectively. The stimulation device control circuit 210 may output a signal CS2 corresponding to the signal CS1 of FIG. 2, and the biosignal sensing device 240 may output a signal SS2 corresponding to the signal SS1 of FIG. 2. The pixel circuit 200 may further include a reference voltage electrode circuit 250.

The reference voltage electrode circuit 250 may generate reference voltages Vref1 and Vref2 that are used in the operations of the stimulation device control circuit 210 and the sensing device control circuit 230. Alternatively, the reference voltage electrode circuit 250 may receive the reference voltages Vref1 and Vref2 that are used in the operations of the stimulation device control circuit 210 and the sensing device control circuit 230 from other electronic device (e.g., a voltage generator, etc.) external to the pixel circuit 200.

As an example, the reference voltages Vref1 and Vref2 may have a high PVT variation (Process Voltage Temperature variation) characteristic. The reference voltage electrode circuit 250 may provide the generated/received reference voltage Vref1 to the stimulation device control circuit 210, and may provide the generated/received reference voltage Vref2 to the sensing device control circuit 230.

The reference voltage Vref1 may be used to control the biosignal stimulation device 220 by the stimulation device control circuit 210. For example, the stimulation device control circuit 210 may adjust characteristic values of the transmitting signal LB1 to be radiated from the biosignal stimulation device 220, based on the reference voltage Vref1. For example, the stimulation device control circuit 210 may adjust a level of the transmitting signal LB1, based on a reference level of the reference voltage Vref1.

The reference voltage Vref2 may be used to process the signal SS2 that is received from the biosignal sensing device 240 by the sensing device control circuit 230. For example, the sensing device control circuit 230 may compare the reference level of the reference voltage Vref2 with a level of the signal SS2 and may obtain a comparison result. For example, the obtained comparison result may be used later to analyze data of the receiving signal LB2 by being provided to the processor, etc. external to the pixel circuit 200.

Figure 6:
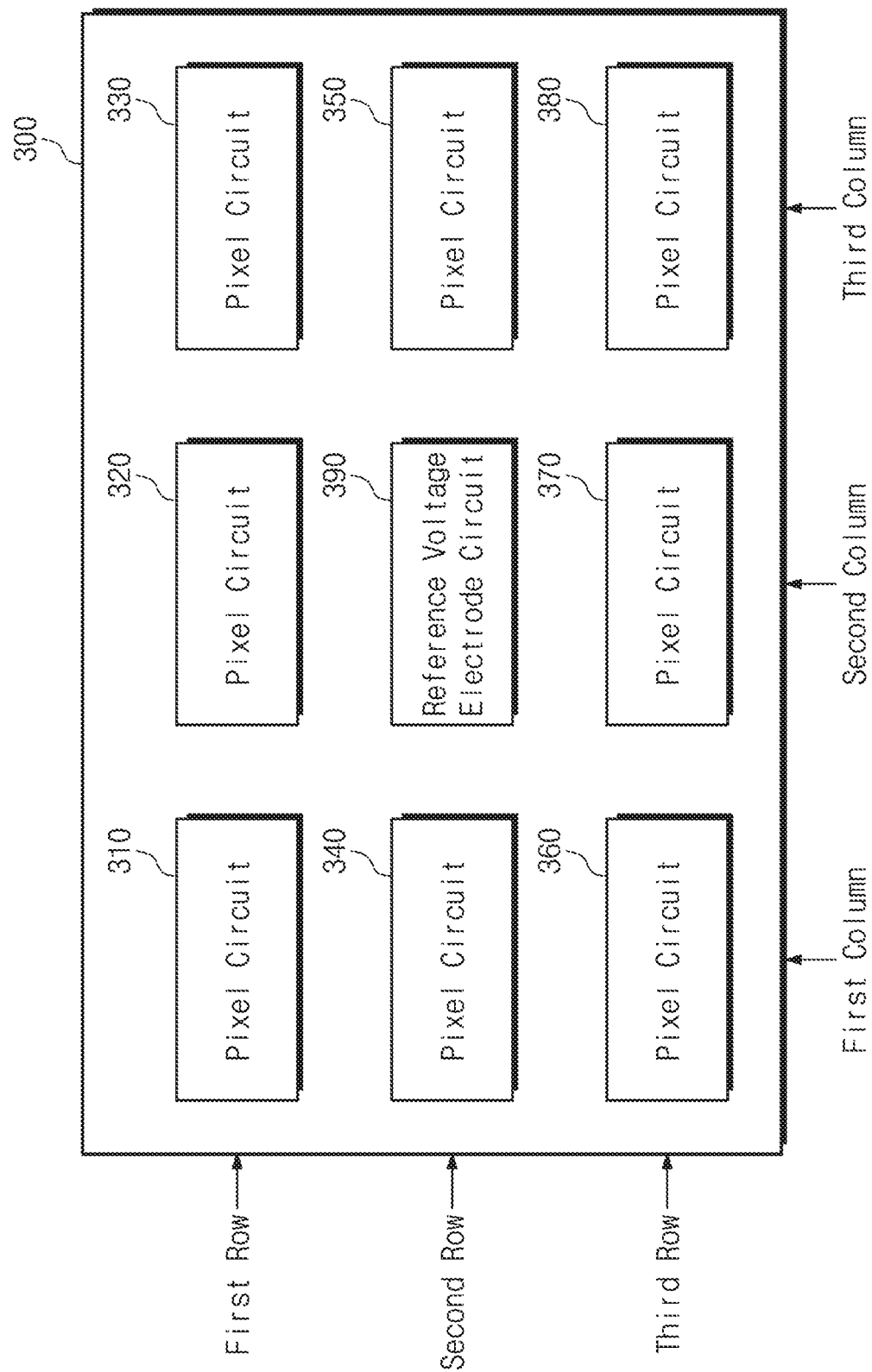
FIG. 6 is a block diagram illustrating an exemplary configuration of a pixel block according to an embodiment of the inventive concept.

FIG. 6 is a block diagram illustrating an exemplary configuration of a pixel block according to an embodiment of the inventive concept.

Referring to FIG. 6, a pixel block 300 may include pixel circuits 310 to 380 and a reference voltage electrode circuit 390. Each of the pixel circuits 310 to 380 may include the pixel circuit 100 of FIG. 2. Exemplary configuration and operations of each of the pixel circuits 310 to 380 are similar to those described with reference to the pixel circuit 100 of FIG. 2, and thus, additional description thereof will be omitted to avoid redundancy. The reference voltage electrode circuit 390 may include the reference voltage electrode circuit 250 of FIG. 5. Exemplary configuration and operations of the reference voltage electrode circuit 390 are similar to those described with reference to the reference voltage electrode circuit 250 of FIG. 5, and thus, additional description thereof will be omitted to avoid redundancy.

The pixel circuits 310 to 380 and the reference voltage electrode circuit 390 may be arranged in three columns and three rows. The first row may include the pixel circuits 310 to 330, the second row may include the pixel circuits 340 and 350 and the reference voltage electrode circuit 390, and the third row may include the pixel circuits 360 to 380. The first column may include the pixel circuits 310, 340, and 360, the second column may include the pixel circuits 320 and 370 and the reference voltage electrode circuit 390, and the third column may include the pixel circuits. 330, 350, and 380.

The pixel circuits 310 to 380 may receive the reference voltages (e.g., the reference voltages Vref1 and Vref2 of FIG. 5) from the reference voltage electrode circuit 390. That is, the pixel circuits 310 to 380 may share the reference voltages generated from the reference voltage electrode circuit 390. The pixel circuit 200 of FIG. 5 may include the reference voltage electrode circuit 250 disposed therein, but the reference voltage electrode circuit 390 of FIG. 6 may be disposed separately from the pixel circuits 310 to 380.

Referring to FIG. 6, the pixel block 300 disposed in the "3×3" configuration is described, but the configuration of the pixel block 300 may be variously changed or modified such that any number of pixel circuits share the reference voltage generated from the reference voltage electrode circuit 390 that is separately disposed.

Figure 7:
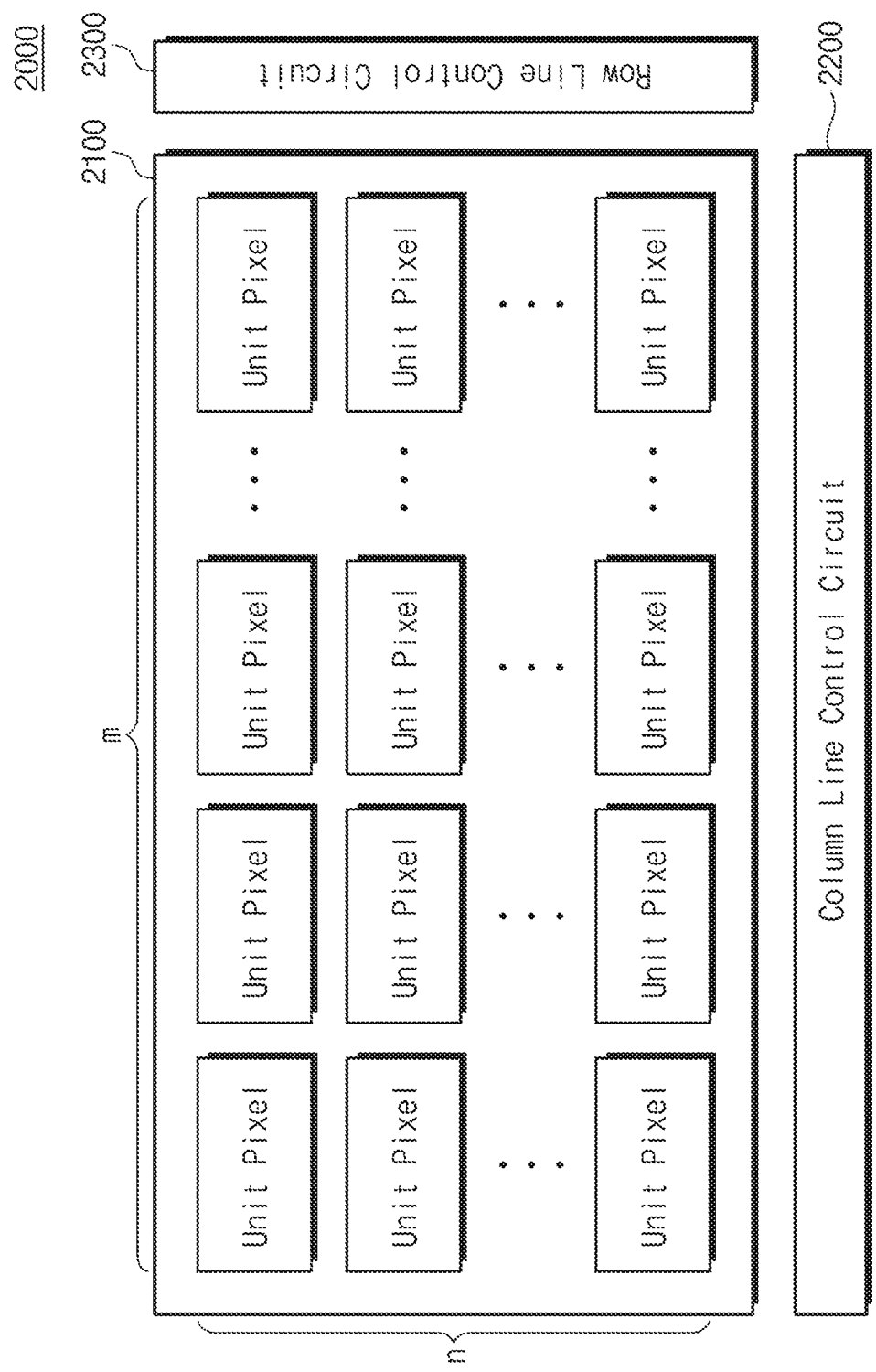
FIG. 7 is a block diagram illustrating an electronic device according to an embodiment of the inventive concept.

FIG. 7 is a block diagram illustrating an electronic device according to an embodiment of the inventive concept.

Referring to FIG. 7, an electronic device 2000 may include an active complex array circuit 2100, a column line control circuit 2200, and a row line control circuit 2300. The active complex array circuit 2100 may include a plurality of unit pixels. The active complex array circuit 2100, the column line control circuit 2200, and the row line control circuit 2300 may be disposed on one substrate.

In an example of FIG. 7, the active complex array circuit 2100 may include unit pixels disposed in an "m×n" configuration. Each of the "n" rows of the active complex array circuit 2100 may include "m" unit pixels. Each of the "m" columns of the active complex array circuit 2100 may include "n" unit pixels. Each of the unit pixels may include at least one of the pixel circuit 100 of FIG. 2, the pixel circuit 200 of FIG. 5, and the pixel block 300 of FIG. 6.

As described with reference to FIG. 2, the unit pixels may be connected to lines (e.g., the line of the selection signal SEL1[k] and the line of the selection signal SEL2[k] of FIG. 2) of a selection signal and lines (e.g., the line of the signal CONT[k] and the line of the signal SEN[k] of FIG. 2) of a signal. The column line control circuit 2200 may output signals for controlling the biosignal stimulation devices and the biosignal sensing devices included in each of the unit pixels to the stimulation device control circuits.

The row line control circuit 2300 may output selection signals for selecting a biosignal stimulation device that is a target to be operated among biosignal stimulation devices that are included in the unit pixels through lines of the selection signal. The row line control circuit 2300 may output selection signals for selecting a biosignal sensing device that is a target to be operated among biosignal sensing devices that are included in the unit pixels through lines of the selection signal.

As an example, a processor external to the electronic device 2000 may control the row line control circuit depending on various logic for controlling the active complex array circuit 2100. Under control of the processor, the row line control circuit 2300 may allow the active complex array circuit 2100 to operate in units of a row. For example, the row line control circuit 2300 may output the selection signals such that "n" rows sequentially operate.

In more detail, the row line control circuit 2300 may sequentially output the select signals having the logic value "1" to the "n" rows such that operations of the pixel circuit 100 of FIG. 2, operations of the pixel circuit 200 of FIG. 5, and operations of pixel block 300 of FIG. 6 are performed sequentially by the unit pixels that are included in the "n" rows.

As an example, "m" unit pixels included in "i"-th row may be selected as the target pixels. In this case, the row line control circuit 2300 may output a selection signal (e.g., the selection signal such as the selection signal SEL1[k] of FIG. 2) having the logic value "1" to biosignal stimulation devices of the unit pixels that are included in the "i"-th row. In addition, the row line control circuit 2300 may output a selection signal (e.g., the selection signal such as the selection signal SEL2[k] of FIG. 2) having the logic value "1" to biosignal sensing devices of the unit pixels that are included in the "i"-th row.

The selection signal for selecting the biosignal stimulation devices and the selection signal for selecting the biosignal sensing devices may be output for different time intervals. For example, the selection signal may be output to the biosignal stimulation devices of the target pixels during a first time interval, and the selection signal may be output to the biosignal sensing devices of the target pixels during a second time interval after the first time interval.

Figure 8:
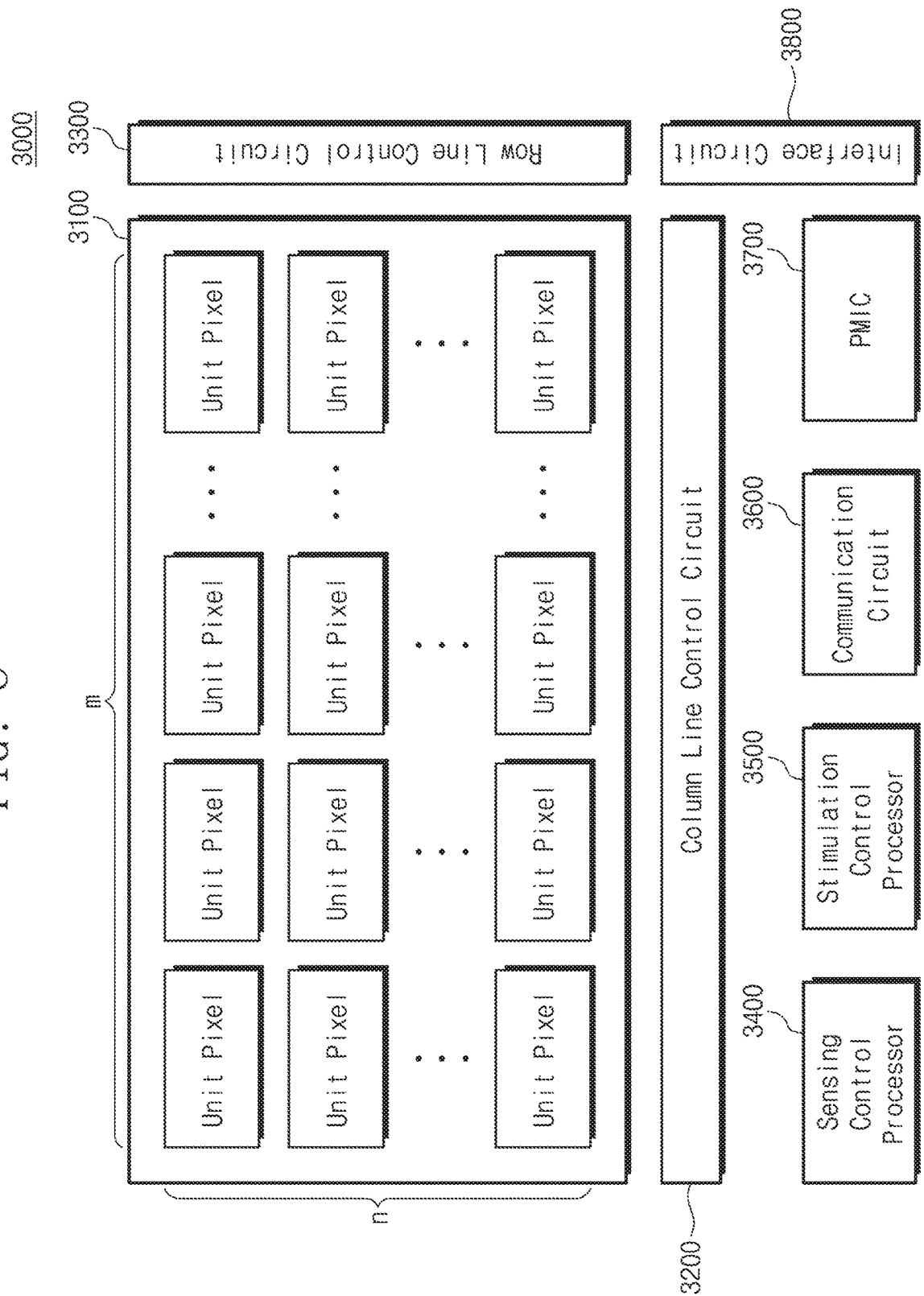
FIG. 8 is a block diagram illustrating an electronic device according to an embodiment of the inventive concept.

FIG. 8 is a block diagram illustrating an electronic device according to an embodiment of the inventive concept.

Referring to FIG. 8, an electronic device 3000 may include an active complex array circuit 3100, a column line control circuit 3200, a row line control circuit 3300, a sensing control processor 3400, a stimulation control processor 3500, a communication circuit 3600, a PMIC 3700, and an interface circuit 3800. The active complex array circuit 3100, the column line control circuit 3200, the row line control circuit 3300, the sensing control processor 3400, the stimulation control processor 3500, the communication circuit 3600, the PMIC 3700, and the interface circuit 3800 may be disposed on one substrate.

However, components of the electronic device 3000 are not limited to an embodiment of FIG. 8. The electronic device 3000 may not include one or more of the components illustrated in FIG. 8, or may further include at least one component not illustrated in FIG. 8.

Comparing FIG. 7 with FIG. 8, exemplary configurations and operations of the active complex array circuit 3100, the column line control circuit 3200, and the row line control circuit 3300 of FIG. 8 are similar to those of the active complex array circuit 2100, the column line control circuit 2200, and the row line control circuit 2300 of FIG. 7, and thus, additional description thereof will be omitted below to avoid redundancy.

As an example, the electronic device 3000 may be wirelessly controlled by a user. When the electronic device 3000 is wirelessly controlled, for efficient operation of the electronic device 3000 (e.g., for real time control of the active complex array circuit 3100), the sensing control processor 3400 and the stimulation control processor 3500 may be integrated with the active complex array circuit 3100, the column line control circuit 3200, and the row line control circuit 3300. For wireless control of the electronic device 3000, the communication circuit 3600, the PMIC 3700, and the interface circuit 3800 may be integrated with the active complex array circuit 3100, the column line control circuit 3200, and the row line control circuit 3300.

The sensing control processor 3400 may control/manage overall operations of the biosignal sensing circuits that are included in the unit pixels. The stimulation control processor 3500 may control/manage overall operations of the biosignal stimulation circuits that are included in the unit pixels. For example, the sensing control processor 3400 and the stimulation control processor 3500 may be implemented as a general purpose processor, a dedicated processor, or an application processor.

For better understanding, in FIG. 8, although the sensing control processor 3400 and the stimulation control processor 3500 are illustrated as separate components, it will be appreciated that the electronic device 3000 may include any number of processors that are configured to perform operations of the sensing control processor 3400 and the stimulation control processor 3500, which will be described below with reference to FIG. 8.

The sensing control processor 3400 may process various calculations based on signals that are received from the biosignal sensing circuits that are included in the unit pixels. The sensing control processor 3400 may process data obtained based on the signal SEN[k] received from the pixel circuit 100 of FIG. 2, and may obtain information related to the object 10 from the processed data. As an example, the sensing control processor 3400 may obtain information related to the active state of the brain, based on the signal SEN[k] that represents information included in the receiving signal LB2 (e.g., the brain wave).

The stimulation control processor 3500 may process various calculations for controlling the biosignal stimulation devices that are included in the unit pixels. The stimulation control processor 3500 may calculate appropriate characteristic values of the transmitting signal LB1 (e.g., ultrasound, light, etc.) to achieve a purpose intended by the user. As an example, the stimulation control processor 3500 may calculate an appropriate frequency and magnitude of the ultrasound to achieve a treatment purpose for the living body.

The communication circuit 3600 may exchange signals with another electronic device/an electronic device/a system, etc. external to the electronic device 3000. As an example, the communication circuit 3600 may process the signals exchanged with another semiconductor chip/an electronic device/a system, etc. external to the electronic device 3000, based on wireless communication protocols such as, Long Term Evolution (LTE), Worldwide Interoperability for Microwave Access (WIMAX), Global System for Mobile communication (GSM), Code Division Multiple Access (CDMA), Bluetooth, Near Field Communication (NFC), Wi-Fi (Wireless Fidelity), Radio Frequency Identification (RFID), etc.

The interface circuit 3800 may mediate communication between the user and the electronic device 3000. For example, the user may input a command to the electronic device 3000 through the interface circuit 3800. The electronic device 3000 may provide information generated by the sensing control processor 3400 and the stimulation control processor 3500 to the user through the interface circuit 3800.

As an example, the interface circuit 3800 may provide the user with information (e.g., information related to the active state of the brain) obtained by the sensing control processor 3400. The user may perform various studies or diagnose a disease, based on the information provided through the interface circuit 3800. For example, the user may input a command for generating the ultrasound through the interface circuit 3800 for the purpose of treating the human body.

The PMIC 3700 may supply power to components of the electronic device 3000. For example, the PMIC 3700 may appropriately convert power received from a battery and/or an external power source, and transfer the converted power to the components of the electronic device 3000.

Figure 9:
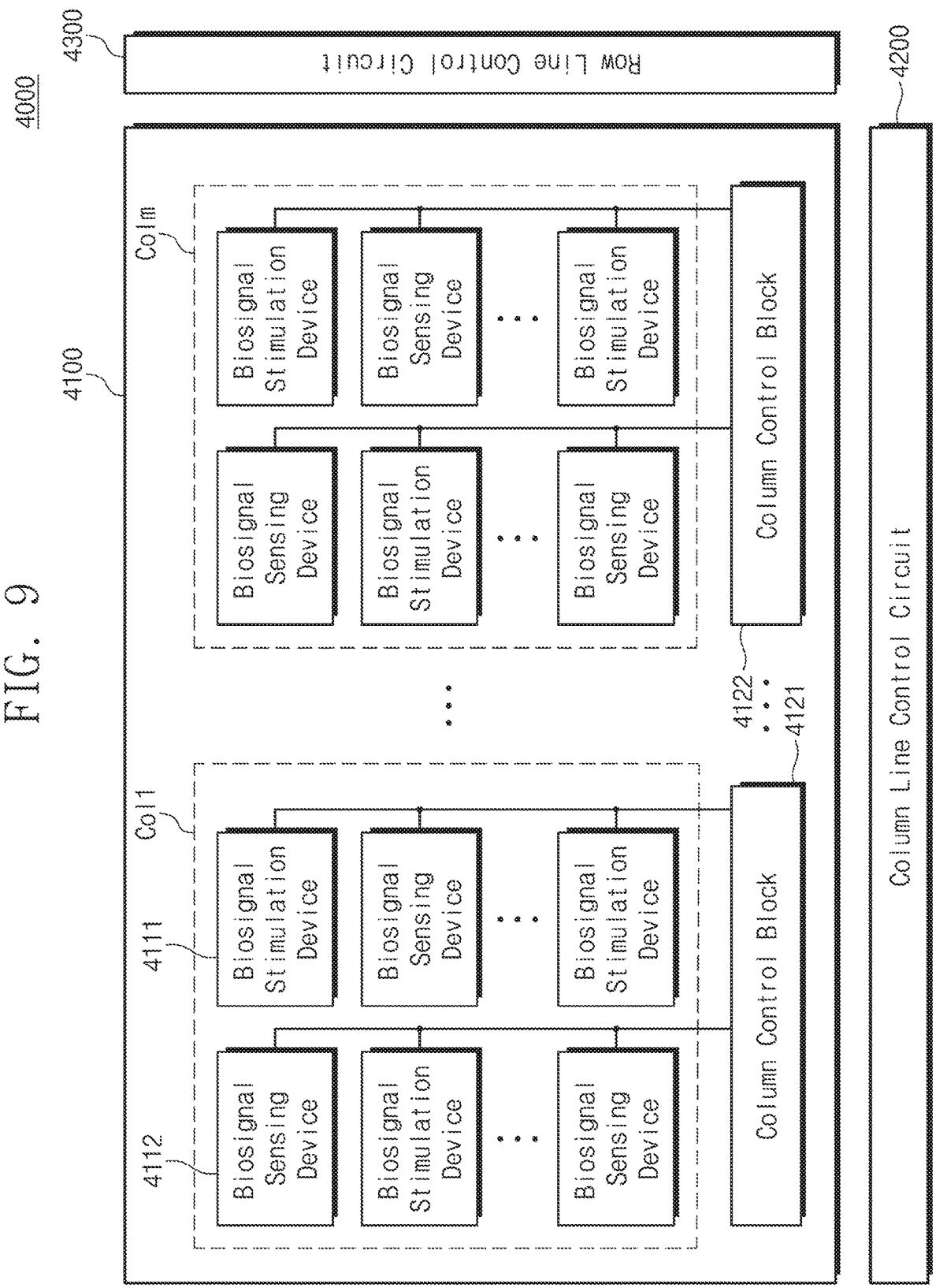
FIG. 9 is a block diagram illustrating an electronic device according to an embodiment of the inventive concept.

FIG. 9 is a block diagram illustrating an electronic device according to an embodiment of the inventive concept.

Referring to FIG. 9, an electronic device 4000 may include an active complex array circuit 4100, a column line control circuit 4200, and a row line control circuit 4300. The active complex array circuit 4100 may include "m" columns Col1 to Colm and "m" column control blocks 4121 to 4122.

Each of the biosignal stimulation devices of FIG. 9 including a biosignal stimulation device 4111 may include the biosignal stimulation device 120 of FIG. 2. Each of the biosignal sensing devices of FIG. 9 including a biosignal sensing device 4112 may include the biosignal sensing device 140 of FIG. 2. Each of the column control blocks of FIG. 9 including the column control blocks 4121 and 4122 may include the stimulation device control circuit 110 and the sensing device control circuit 130 of FIG. 2.

The biosignal sensing devices and the biosignal stimulation devices may be controlled in units of a column by the column control blocks 4121 to 4122. For example, the biosignal sensing devices and the biosignal stimulation devices of the column Col1 are collectively controlled by the column control block 4121, and the biosignal sensing devices and the biosignal stimulation devices of the column Colm may be collectively controlled by the column control block 4122.

As described with reference to FIG. 2, the biosignal sensing devices and the biosignal stimulation devices may include passive devices. In contrast, the column control blocks 4121 to 4122 may include active devices (e.g., electronic circuits including a plurality of transistors) for controlling the biosignal sensing devices and the biosignal stimulation devices.

As will be described with reference to FIG. 10, the biosignal sensing devices and the biosignal stimulation devices of the columns Col1 to Colm including the passive devices and the column control blocks 4121 to 4122 including the active devices may be disposed in separate regions, respectively.

Figure 10:
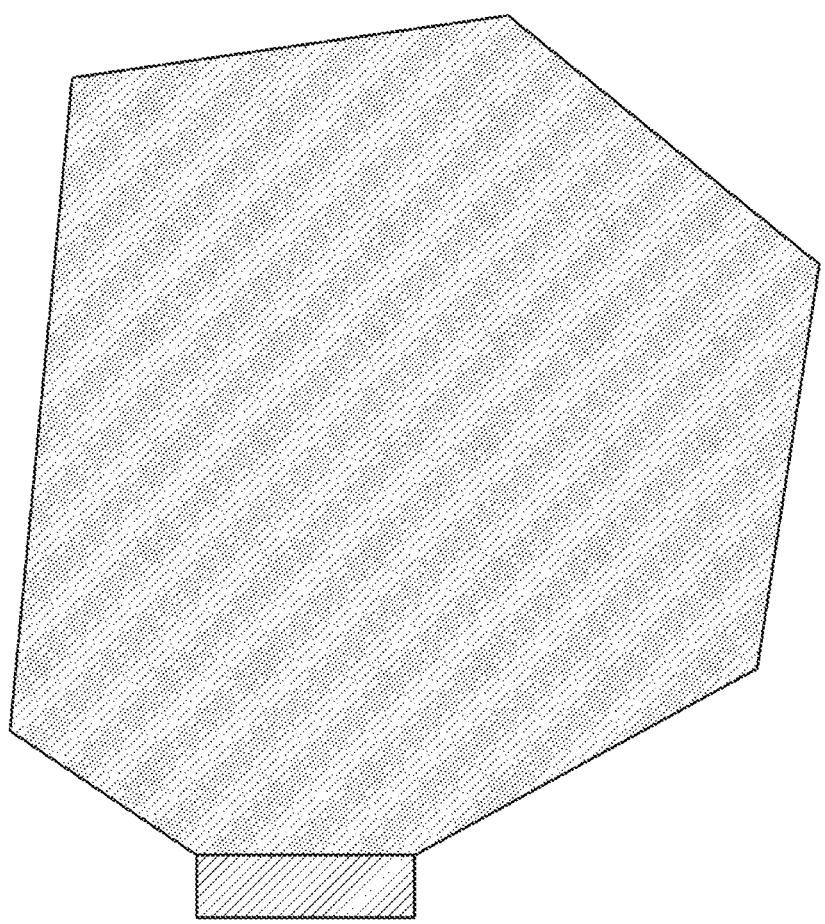
FIG. 10 is a conceptual diagram illustrating an electronic device according to an embodiment of the inventive concept.

FIG. 10 is a conceptual diagram illustrating an electronic device according to an embodiment of the inventive concept.

Referring to FIG. 10, an electronic device 5000 may include an active complex array having an indeterminate form. For example, the electronic device 5000 may include the electronic device 4000 of FIG. 9.

As described with reference to FIG. 9, the biosignal sensing devices and the biosignal stimulation devices including the passive devices, and the column control blocks including the active devices may be disposed in separate regions, respectively. In an example of FIG. 10, the biosignal sensing devices and the biosignal stimulation devices of the columns Col1 to Colm may be disposed in a first region, and the column control blocks 4121 to 4122 may be disposed in a second region.

The column control blocks may include various configurations (e.g., wires for receiving operating voltages) for operating the active devices. In contrast, configurations of the biosignal sensing devices and the biosignal stimulation devices including the passive devices may be simpler than those of the column control blocks. Accordingly, the biosignal sensing devices and the biosignal stimulation devices may be easily disposed in a region of the indeterminate form, and the column control blocks may be difficult to be disposed in the region of the indeterminate form.

Like the active complex array circuit 4100 of FIG. 9, in the case where the active devices and the passive devices are respectively disposed in separate regions, the biosignal sensing devices and the biosignal stimulation devices included in the columns Col1 to Colm may be disposed on a region (e.g., the first region) of an indeterminate form, and the column control blocks may be disposed on another region (e.g., the second region). That is, a designer may easily design the electronic device 5000 including an active complex array circuit having an indeterminate form by designing according to the arrangement of the active complex array circuit 4100.

According to an embodiment of the inventive concept, a pixel circuit and an electronic device configured to radiate a signal for stimulating a living body and to receive a biosignal may be designed with a relatively high degree of integration.

The contents described above are specific embodiments for implementing the inventive concept. The inventive concept may include not only the embodiments described above but also embodiments in which a design is simply or easily capable of being changed. In addition, the inventive concept may also include technologies easily changed to be implemented using embodiments. Therefore, the scope of the inventive concept is not limited to the described embodiments but should be defined by the claims and their equivalents.

What is claimed is:

1. A pixel circuit comprising:
    a sensing circuit configured to output biometric data of a biosignal, and including a biosignal sensing device and a sensing device control circuit;
    a stimulation circuit configured to radiate a stimulation signal, and including a biosignal stimulation device and a stimulation device control circuit;
    a first line control circuit configured to output a first selection signal for selecting the sensing circuit as a target sensing circuit, and to output a second selection signal for selecting the stimulation circuit as a target stimulation circuit;
    a reference voltage electrode circuit configured to generate a first reference voltage and a second reference voltage respectively associated with radiating the stimulation signal and receiving the biosignal, wherein the pixel circuit is configured to radiate the stimulation signal in response to a first logic value of the first selection signal and to output biometric data of the biosignal in response to a second logic value of the second selection signal; and
    a second line control circuit configured to process characteristic data associated with the biometric data and the stimulation signal,
    wherein
    the sensing circuit includes a first transistor that is turned on or off based on the first selection signal,
    the stimulation circuit includes a second transistor that is turned on or off based on the second selection signal,
    the sensing device control circuit is coupled to the first transistor,
    the stimulation device control circuit is coupled the second transistor,
    the stimulation device control circuit is configured to, based on the first reference voltage and states of the first transistor and the second transistor, adjust a characteristic value of the stimulation signal, and
    the sensing device control circuit is configured to, based on the second reference voltage and states of the first transistor and the second transistor, process a signal received from the biosignal sensing device.

2. The pixel circuit of claim 1, wherein the stimulation circuit is further configured to receive a first signal that indicates the characteristic data in response to the second selection signal.

3. The pixel circuit of claim 1, wherein the sensing circuit, the stimulation circuit, the first line control circuit, and the second line control circuit are disposed on one substrate.

4. An electronic device comprising:
a pixel array circuit configured to radiate a stimulation signal by a target pixel that is selected in response to a first logic value of a first selection signal, and to output biometric data of a biosignal by the target pixel that is selected in response to a second logic value of a second selection signal; and
a first line control circuit configured to generate the first selection signal and the second selection signal,
wherein the pixel array circuit and the first line control circuit are disposed on one substrate,
wherein the target pixel includes:
  a sensing circuit configured to output the biometric data, and including a biosignal sensing device and a sensing device control circuit;
  a stimulation circuit configured to radiate the stimulation signal, and including a biosignal stimulation device and a stimulation device control circuit;
  a reference voltage electrode circuit configured to generate a first reference voltage and a second reference voltage respectively associated with radiating the stimulation signal and receiving the biosignal,
  a first transistor that is turned on or off based on the first selection signal, and
  a second transistor that is turned on or off based on the second selection signal, and
wherein
  the sensing device control circuit is coupled to the first transistor,
  the stimulation device control circuit is coupled the second transistor,
  the stimulation device control circuit is configured to, based on the first reference voltage and states of the first transistor and the second transistor, adjust a characteristic value of the stimulation signal, and
  the sensing device control circuit is configured to, based on the second reference voltage and states of the first transistor and the second transistor, process a signal received from the biosignal sensing device.

5. The electronic device of claim 4, wherein the one substrate is a thin film transistor (TFT) substrate.

6. The electronic device of claim 4, further comprising a first processor configured to control the first line control circuit such that the first selection signal has the first logic value during a first time interval and the second selection signal has the second logic value during a second time interval, and configured to be disposed on the same substrate as the pixel array circuit and the first line control circuit.

7. The electronic device of claim 6, wherein the first time interval does not overlap with the second time interval.

8. The electronic device of claim 4, further comprising:
a second line control circuit configured to process the biometric data and to output a signal for controlling an operation of the target pixel.

9. The electronic device of claim 4, further comprising a second processor configured to obtain information associated with the biosignal based on the biometric data, and configured to be disposed on the same substrate as the pixel array circuit and the first line control circuit.

10. An electronic device comprising:
a unit pixel including a reference voltage electrode circuit configured to generate a first reference voltage and a second reference voltage respectively associated with radiating a stimulation signal and receiving a biosignal, and a plurality of pixel circuits configured to radiate the stimulation signal in response to a first logic value of a first selection signal and to output biometric data of the biosignal in response to a second logic value of a second selection signal; and
a line control circuit configured to output the first selection signal and the second selection signal for selecting the unit pixel as a target pixel,
wherein the first reference voltage and the second reference voltage are shared by the plurality of pixel circuits such that the stimulation signal is radiated and the biometric data are processed,
wherein the plurality of pixel circuits includes a first transistor that is turned on or off based on the first selection signal and a second transistor that is turned on or off based on the second selection signal,
wherein the unit pixel includes:
  a biosignal sensing device;
  a sensing device control circuit coupled to the biosignal sensing device;
  a biosignal stimulation device; and
  a stimulation device control circuit coupled to the biosignal stimulation device; and
wherein
  the reference voltage electrode circuit is (i) coupled to the stimulation device control circuit and the sensing device control circuit and (ii) is configured to supply the first reference voltage to the stimulation device control circuit and supply the second reference voltage to the sensing device control circuit,
  the sensing device control circuit is coupled to the first transistor,
  the stimulation device control circuit is coupled the second transistor,
  the stimulation device control circuit is configured to, based on the first reference voltage and states of the first transistor and the second transistor, adjust a characteristic value of the stimulation signal, and
  the sensing device control circuit is configured to, based on the second reference voltage and states of the first transistor and the second transistor, process a signal received from the biosignal sensing device.

* * * * *